US008870734B2

(12) United States Patent
Eberle et al.

(10) Patent No.: US 8,870,734 B2
(45) Date of Patent: Oct. 28, 2014

(54) CARTRIDGE AND CENTRIFUGE HAVING A CARTRIDGE

(75) Inventors: Klaus-Günter Eberle, Tuttlingen (DE); Roland Biset, Leuven (BE)

(73) Assignees: Terumo BCT, Inc., Lakewood, CO (US); Andreas Hettich GmbH & Co. KG, Tuttlingen (DE)

( * ) Notice: Subject to any disclaimer, the term of this patent is extended or adjusted under 35 U.S.C. 154(b) by 901 days.

(21) Appl. No.: 12/602,952

(22) PCT Filed: Jun. 4, 2008

(86) PCT No.: PCT/EP2008/056926
§ 371 (c)(1),
(2), (4) Date: Mar. 1, 2010

(87) PCT Pub. No.: WO2008/148811
PCT Pub. Date: Dec. 11, 2008

(65) Prior Publication Data
US 2010/0170858 A1 Jul. 8, 2010

(30) Foreign Application Priority Data
Jun. 5, 2007 (DE) .......................... 10 2007 000 308

(51) Int. Cl.
*B04B 7/12* (2006.01)
*B04B 5/04* (2006.01)
*A61M 1/36* (2006.01)
*A61M 1/02* (2006.01)

(52) U.S. Cl.
CPC ................. *B04B 5/0428* (2013.01); *B04B 7/12* (2013.01); *A61M 1/3693* (2013.01); *B04B 2005/0435* (2013.01); *B04B 2005/0478* (2013.01); *A61M 1/0227* (2014.02); *A61M 1/0277* (2014.02); *A61M 1/3698* (2014.02)
USPC .................................. 494/45; 494/10; 494/26

(58) Field of Classification Search
CPC B04B 5/0428; B04B 7/12; B04B 2005/0435; B04B 2005/0478; A61M 1/0227; A61M 1/0277; A61M 1/3693; A61M 1/3698

USPC ........... 494/45, 10, 26, 43; 210/781, 782, 789
See application file for complete search history.

(56) References Cited

U.S. PATENT DOCUMENTS 5,543,062 A 8/1996 Nishimura
5,734,464 A 3/1998 Gibbs
(Continued)

FOREIGN PATENT DOCUMENTS

EP 0499891 A1 8/1992
EP 0616816 A2 9/1994
(Continued)

OTHER PUBLICATIONS

International Search Report dated Sep. 25, 2008 for PCT/EP2008/056926.
(Continued)

*Primary Examiner* — Timothy Cleveland
(74) *Attorney, Agent, or Firm* — John R. Merkling

(57) ABSTRACT

The invention relates to a cartridge (1) for accommodating blood bags (35), which is provided for the separation of blood components for the application in a centrifuge. The cartridge (1) has a partition wall (3) which separates a blood bag section (5) positioned radially inside from a product section (7) positioned radially outside, and a cover (9) disposed in a mounting position above the blood bag section (5). The cover (9) is connected to the partition wall (3) pivotally in a first point (11) and detachably in a second point (13), so that the blood bag section (5) is freely accessible by means of laterally pivoting the cover (9) out of the way. The cartridge is applicable in the rotor of a centrifuge.

20 Claims, 11 Drawing Sheets

(56) References Cited

U.S. PATENT DOCUMENTS

Figure 1:
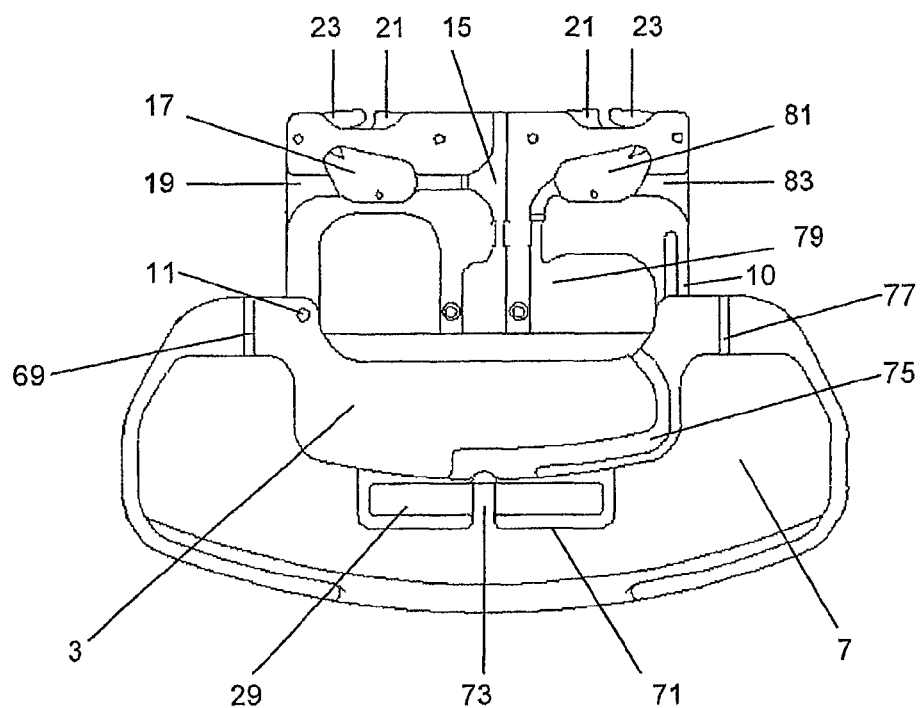

| | | |
|---|---|---|
| 2002/0085957 A1 | 7/2002 | Moore et al. |
| 2003/0176267 A1* | 9/2003 | Eberle .............................. 494/10 |
| 2004/0026341 A1* | 2/2004 | Hogberg et al. .............. 210/782 |
| 2008/0220959 A1* | 9/2008 | Holmes et al. .................. 494/45 |

FOREIGN PATENT DOCUMENTS

| | | |
|---|---|---|
| EP | 1351772 B1 | 12/2001 |
| EP | 1512464 A2 | 3/2005 |
| GB | 2174149 A | 10/1986 |
| WO | 02053292 A1 | 7/2002 |
| WO | 03089027 A2 | 10/2003 |
| WO | WO 2007024550 A2 * | 3/2007 |

OTHER PUBLICATIONS

International Search Report dated Sep. 25, 2008 for PCT/EP2008/056923.

International Search Report dated Oct. 14, 2008 for PCT/EP2008/056925.

* cited by examiner

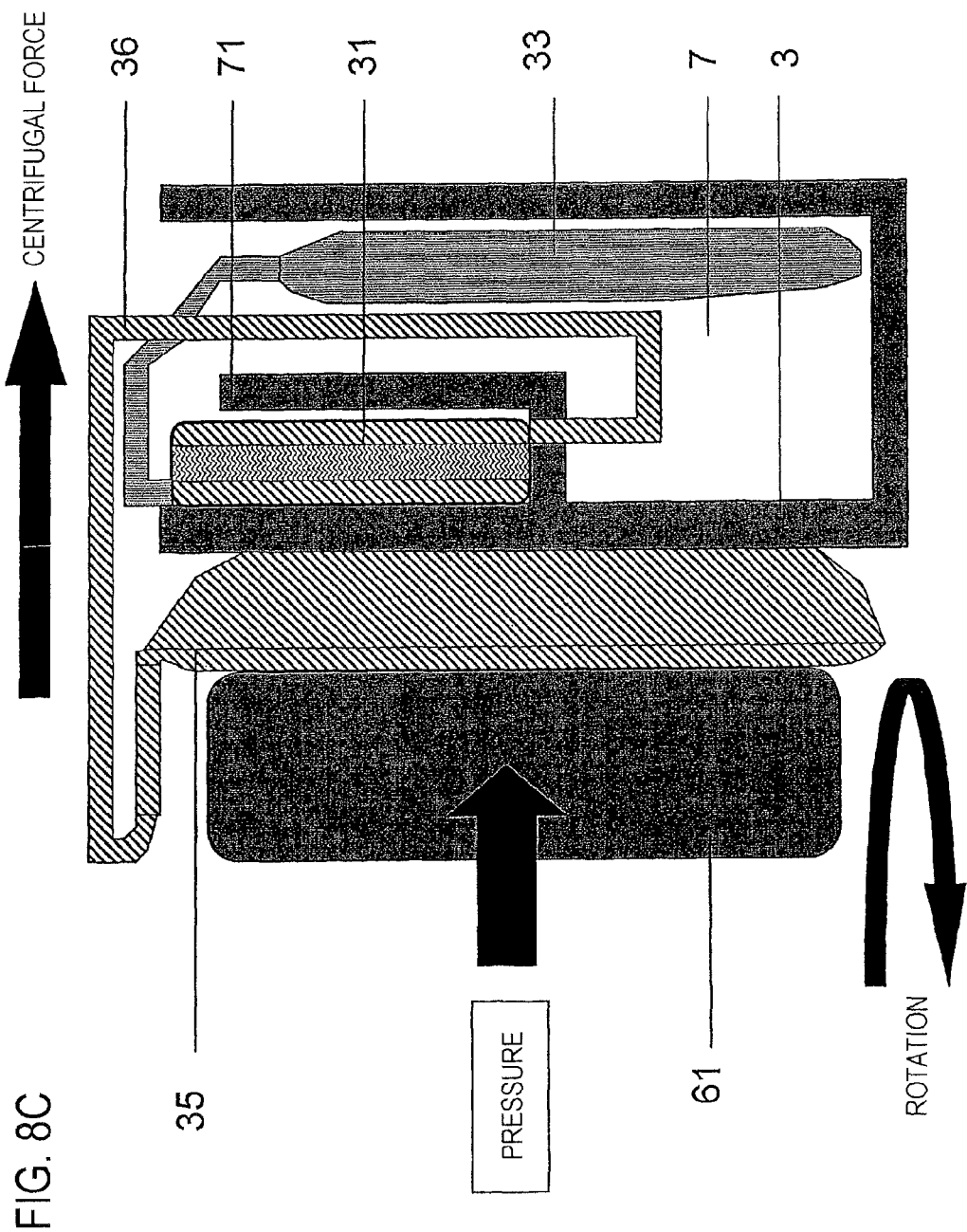

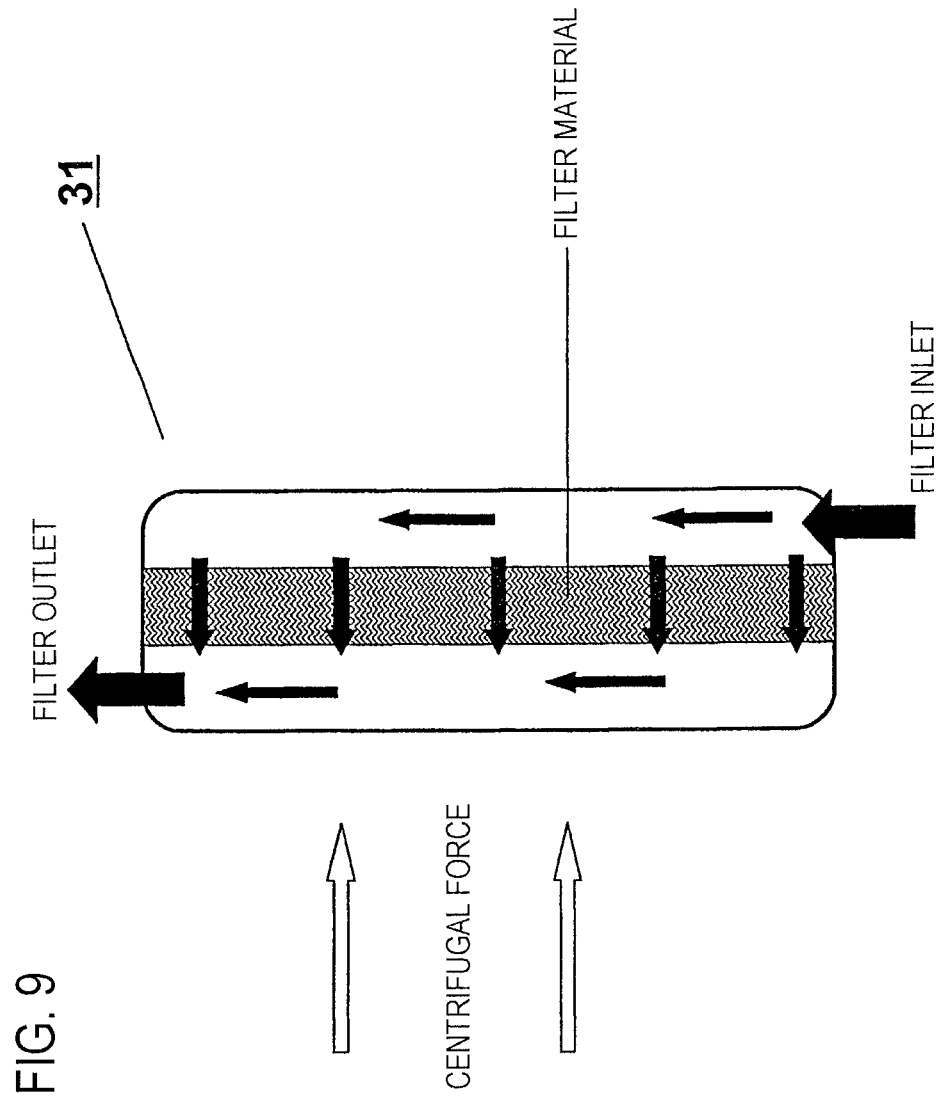

CARTRIDGE AND CENTRIFUGE HAVING A CARTRIDGE

TECHNICAL FIELD

The invention relates to a cartridge which is in particular provided for the application in a centrifuge in order to separate blood into its components, and to a centrifuge having such a cartridge.

STATE OF THE ART

In transfusion medicine the so-called blood component therapy has established itself since the beginning of the nineties. This means that instead of a whole blood conserve only those blood components are administered to a patient that the individual patient requires. By means of this separate administering of the individual blood components, it is possible that one single blood conserve can provide optimal help to an average of 1.8 patients.

The essential blood components are
- the red blood cells in the so-called erythrocyte concentrate which are transfused in order to maintain the oxygen supply after severe loss of blood.
- the blood platelets in the thrombocyte concentrate which are administered in cases of coagulation disturbances (haemophilia), and
- the blood plasma which is administered in cases of coagulation disturbances and volume deficits. Apart therefrom, blood plasma is an essential basic component for the production of many medicaments.

The separation of the individual blood components which is defined as cell isolation is known to be effected by treating the blood in a centrifuge. By means of centrifuging the individual blood components are separated and then each individual one can be filled into the respective containers for further use.

Such centrifuge is for example known from document EP 1 351 772 B1. According to this state of the art, a plurality of cartridges are arranged around a hub in a rotor of a centrifuge. The cartridges are firmly held in the rotor such that the blood bags are centrifuged in an upright position. Inside, the cartridges comprise accommodating devices for accommodating a blood bag containing whole blood and product bags in which the plasma and the erythrocyte concentrate are collected, respectively. In order to avoid a continued flowing and renewed mixing of the products after the individual components have been separated, various clamping means are provided in the cartridge for clamping the individual tubes. Before removing the bags from the cartridge after the separation has been effected, the individual connecting tubes of the bags must be sealed by appropriate measures. Only then can the clamps of the cartridge be opened, the bags be removed and the cartridge get prepared for accommodating a new set of bags.

After the separation and the drawing off of the plasma or the red blood cells, a mixture called "buffy coat" remains in the blood bags. This "buffy coat" consists mainly of platelets as well as white and red blood cells. For obtaining the platelets from this "buffy coat", the latter is diluted with an additive solution and this diluted "buffy coat" is then again separated into its components by centrifuging.

From document WO 03/089027 a system and a method for this purpose are already known. This document discloses a centrifuge in which a ring-shaped bag containing a mixture of "buffy coat" and additive solution is inserted into its single chamber. The blood components are then separated by means of a centrifuging operation and the separated components are transported via a tube line through a filter provided in the area of the hub to a collection container also provided in the area of the hub.

REPRESENTATION OF THE INVENTION

Technical Object

It is the object of the invention to provide an improved cartridge and a centrifuge including the cartridge that allow a more economic cell isolation.

Technical Solution

The object of the invention is achieved by means of a cartridge according to claim 1. Advantageous embodiments of the invention are achieved according to the dependent claims.

A cartridge according to the invention for accommodating blood bags, which is used for the application in a centrifuge in order to separate the blood components, comprises a partition wall and a cover. The partition wall separates a blood bag section positioned radially inside from a product section positioned radially outside. The cover is positioned above the blood bag section in a mounting position of the cartridge. The cover is connected to the partition wall pivotally at a first point, and detachably at a second point. In this way, the blood bag section is freely accessible by means of laterally pivoting the cover out of the way.

This enables a fast changing of the blood bag in the blood bag section. By means of the pivotal connection between the cover and the partition wall one or several connecting tubes of the blood bag can be easily positioned while the cover is being closed. Thus the tubes are optimally fixed within a short period of time.

Advantageously, a recess for holding a tube of the blood bag and/or a tube clamp can be formed in an upper section of the cover. These recesses enable the use of the original blood bags without further measures for preparing the bag or the tube being required.

In the cover an operating device can be provided for operating a tube clamp disposed on a tube of the blood bag. Since the clamps already disposed on the tube can be opened and closed by means of the operating device, it is not necessary to provide separate clamping means with the cartridge.

For an easy operation of the clamp, the operating device can protrude from the cover at a side surface located opposite the partition wall when the cover is closed.

In the recess a sensor can be provided, which can in particular be a photo sensor. Depending on the color of the blood liquid transported through the tube, this enables the execution of respective reactions such as operating the clamp in order to terminate the discharge of the blood liquid from the bag.

At a bottom surface of the cover an electric connection means can be provided for the electric connection with a centrifuge. Thus it is possible to transmit signals from a control device mounted inside the centrifuge to the cartridge and in the reverse direction, respectively.

Furthermore, a fixture for a filter and/or for a product bag can be provided in the product section of the cartridge. Accordingly, after the cover has been opened, the partly or completely emptied blood bag with the remaining content can be removed from the cartridge together with the filter and the product bag which for example contains the plasma or the erythrocyte concentrate.

Advantageously, the fixture may comprise an outside wall which is positioned radially outside the partition wall and which is provided with a guiding means for guiding the tube. The guiding means can be provided as a slot in the outside wall such that the tube can be inserted radially from the outside and from below into the fixture.

Advantageously, this enables that red blood cells that are transported through the tube collect at the outside wall and at the bottom surface of the filter, and that there is no risk that the red blood cells are transported further into the product bag.

At the top surface of the partition wall a recess for guiding the tube from the fixture radially inwards to second recesses in the top surface of the cover can be provided. Said second recesses are provided for holding the tube and a second tube clamp. In particular, these can be provided in an essentially mirror-image manner relative to the first recesses.

At an upper edge, the partition wall can comprise a passage for feeding the tube from the radially inside area of the partition wall to the radially outside area of the partition wall. Among other things, this serves to position the tube and to ensure that the tube leads to the filter radially from the outside and from below.

Advantageously, a second photo sensor can be provided in the second recesses and/or second operating device corresponding to the operating device are provided in the cover for a tube clamp to be held in one of the second recesses. Particularly the second sensor enables the optimization of the yield in cell isolation by means of outputting a final signal for terminating the transportation combined with a signal for closing the tube clamps, after an "attention" signal has been output by the first sensor, starting out from a predetermined composition of the product in the tube.

The cartridge can furthermore be provided with a collecting tank which is positioned radially outwards and which can embrace the product section and parts of the blood bag section. Advantageously, a handling device is provided inside the collecting tank to facilitate the handling of the collecting tank and the cartridge partly embraced thereby. This handling device can be provided for example in the form of finger holes or handles.

The above described cartridge is provided for use in a centrifuge for the separation of blood components. The centrifuge comprises a hub and a rotor which revolves around the hub. Advantageously, in the rotor accommodating boxes are provided around the hub, which are also described as system boxes and which are used for accommodating the cartridges. However, it is also possible to use a centrifuge in which only one cartridge is accommodated. Each cartridge can be removed freely from the accommodating box and, thus, the centrifuge by operating a locking element connected to the accommodating box. These accommodating boxes can be detachably connected to the rotor.

This enables a fast exchanging of the cartridges containing the separated blood components with new cartridges containing blood components which are not yet separated while enabling a better production yield in cell isolation and an optimized equipment utilization.

In its non-operated state the locking element can assume a locking position. Thus an immediate locking is achieved as soon as a cartridge is inserted into the accommodating box of the rotor. The locking element can furthermore be provided in the area of the hub or of the accommodating box.

Furthermore the locking element can be provided at a support assigned to the cartridge. Accordingly, the cartridge is then accommodated between the support and one wall of the accommodating box and can only be moved upwards in one direction. This movement is, however, only possible by an operation of the locking element. This makes a secure positioning of the cartridge in the accommodating box possible for the centrifuging operation.

For holding the cartridge, the locking element in its non-operated state can be engaged with a side surface of the cover, located opposite the partition wall. A projection is formed on the locking element to prevent an upward movement of the cartridge.

The support can furthermore comprise a contact pad for enabling an electrically conductive connection between the accommodating box and the cartridge. The contact pad can consist of a plurality of electric contact points.

At the support a pressing element can be provided so as to be radially movable into the section below the cover. This serves to press the separated components from the blood bag into the tube, through which they are further transported to the filter and into the product bag.

A first section of a line from the blood bag can advantageously lead upwards and radially inwards. This eliminates an undesired escape of liquids into the tube before the blood components are separated from each other.

The invention also relates to a method for cell isolation. The method comprises the following steps: inserting a blood bag containing whole blood into a blood bag section of a cartridge, closing a cover of the blood bag section by pivoting the cover to the side, and positioning a tube of the blood bag, connecting the tube to a filter in a product section of the cartridge, inserting the cartridge into a rotor of a centrifuge by latching a locking element, spinning the centrifuge in order to separate the blood components in the blood bag, applying pressure onto the blood bag by means of a pressing element in order to press a blood component into the tube and further into the filter and into a product bag positioned behind the filter, terminating the pressing and the spinning, operating the locking element and removal of the cartridge, opening the cover and removing the bags containing the separated blood components.

On the one hand, the method according to the invention enables a faster exchanging of the blood bags and product bags with new bags. On the other hand, the possibility to mount and remove the cartridges by one turn of the hand enables an almost continuous performance of the centrifuging and separation processes, since these only need to be interrupted for the changing of the cartridges.

The cartridge and the centrifuge according to the invention are suited for the separation of cells and plasma from whole blood, on the one hand, but are also provided for extracting cells from the "buffy coat" that remains after a known centrifuging operation.

For this purpose, the "buffy coat" from several blood bags is collected together with an additive solution in a new blood bag, and is mixed. The new blood bag corresponds to the blood bag according to the invention. Advantageously, the new blood bag can be provided with a tube and/or a filter, in particular one provided for the filtering of leukocytes.

BRIEF DESCRIPTION OF THE ILLUSTRATIONS OF THE DRAWINGS

Figure 2:
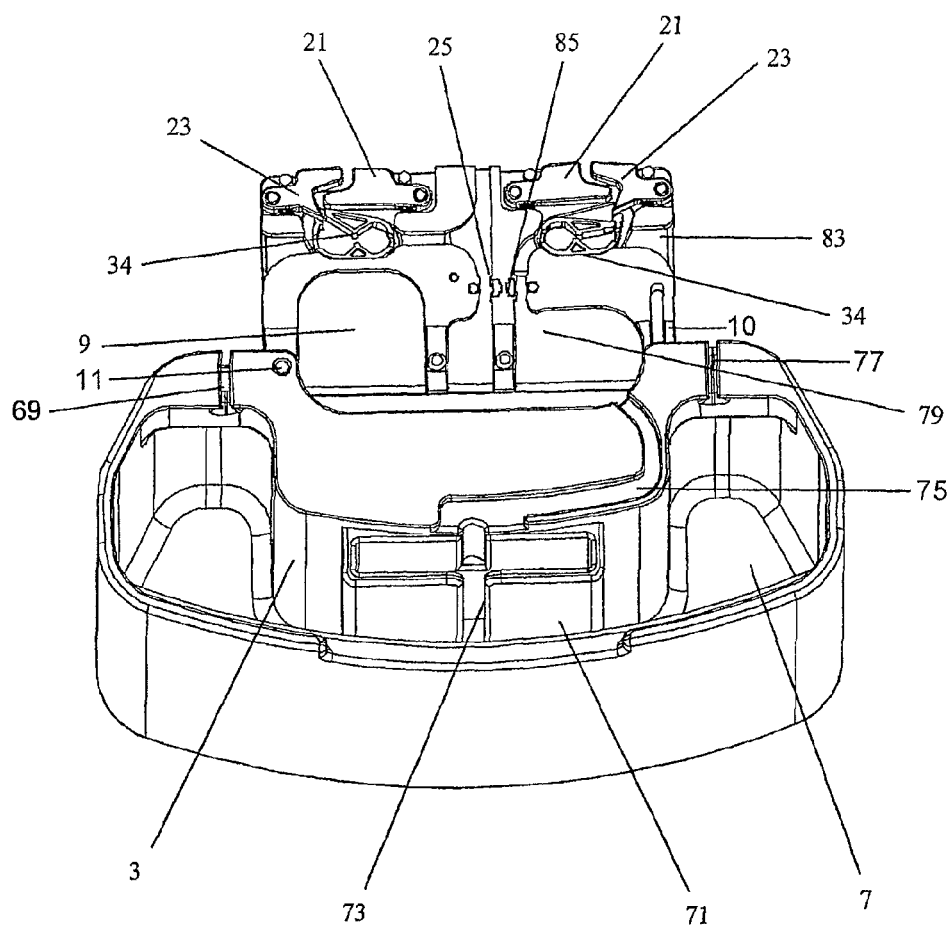
Figure 3:
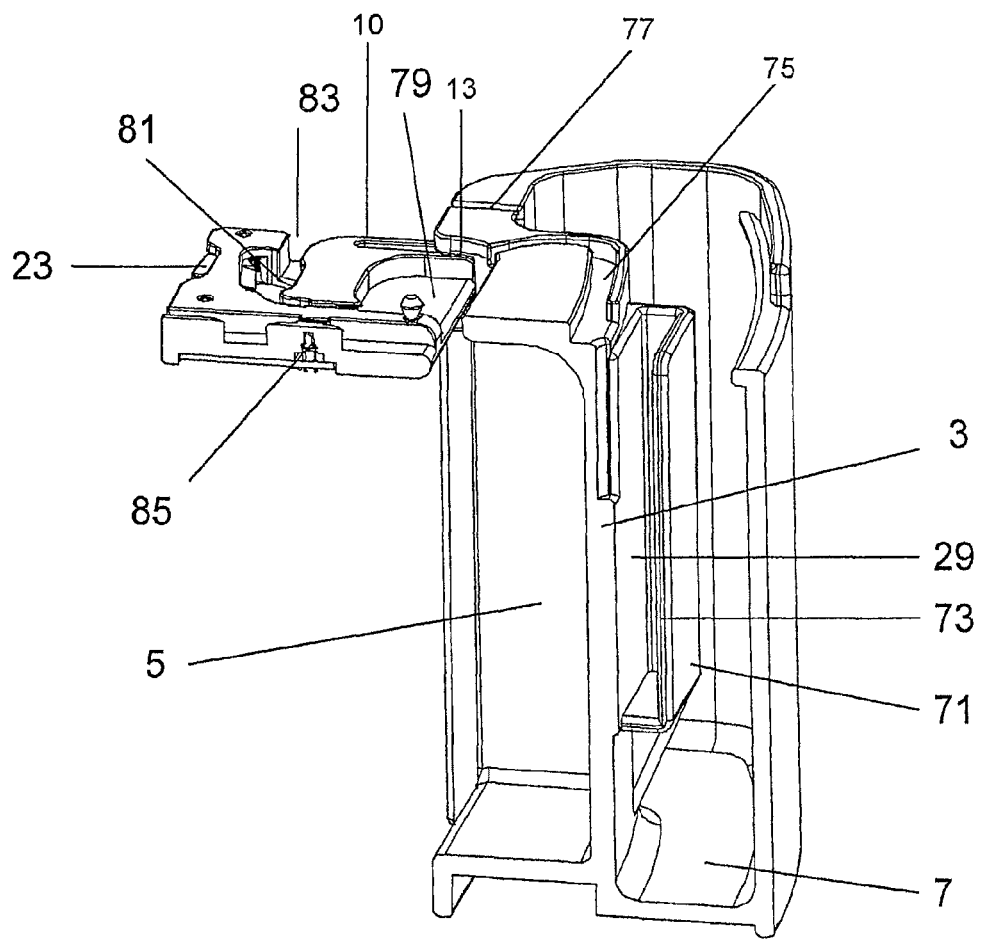
Figure 4:
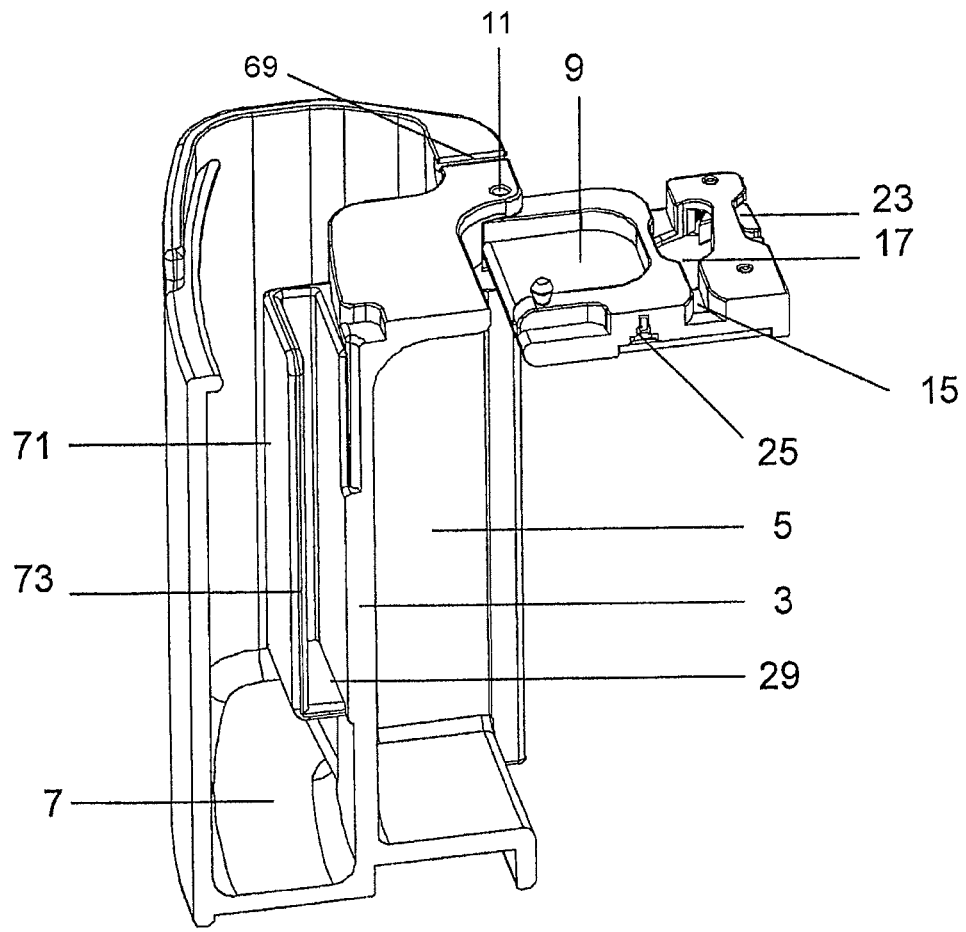
Figure 5:
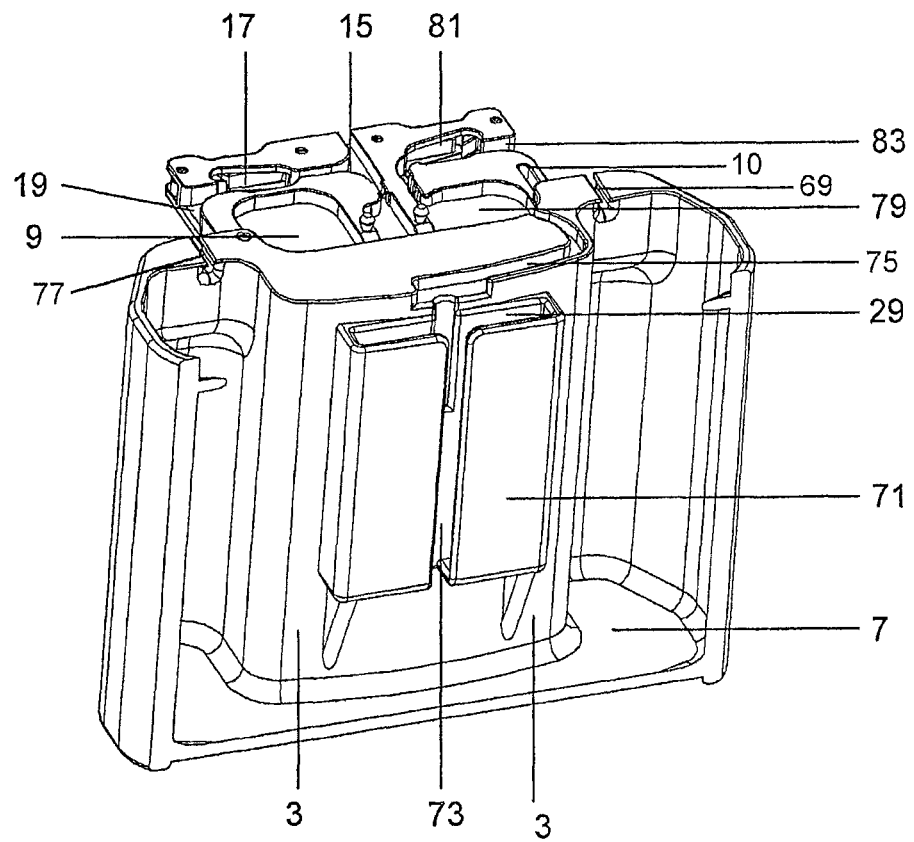
Figure 6:
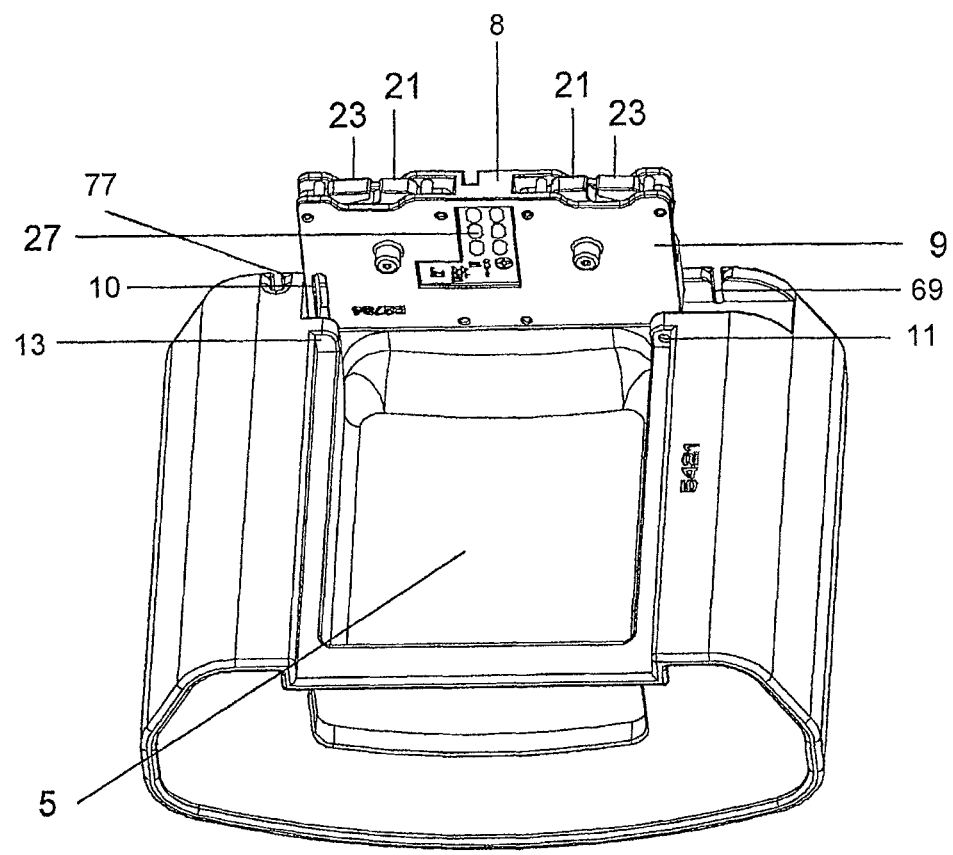
Figure 7:
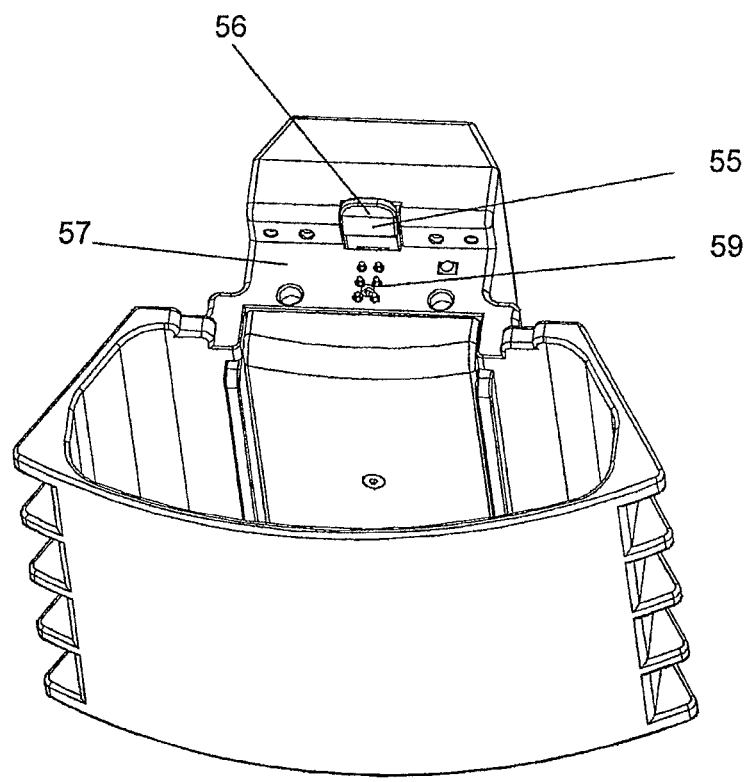
Figure 8A:
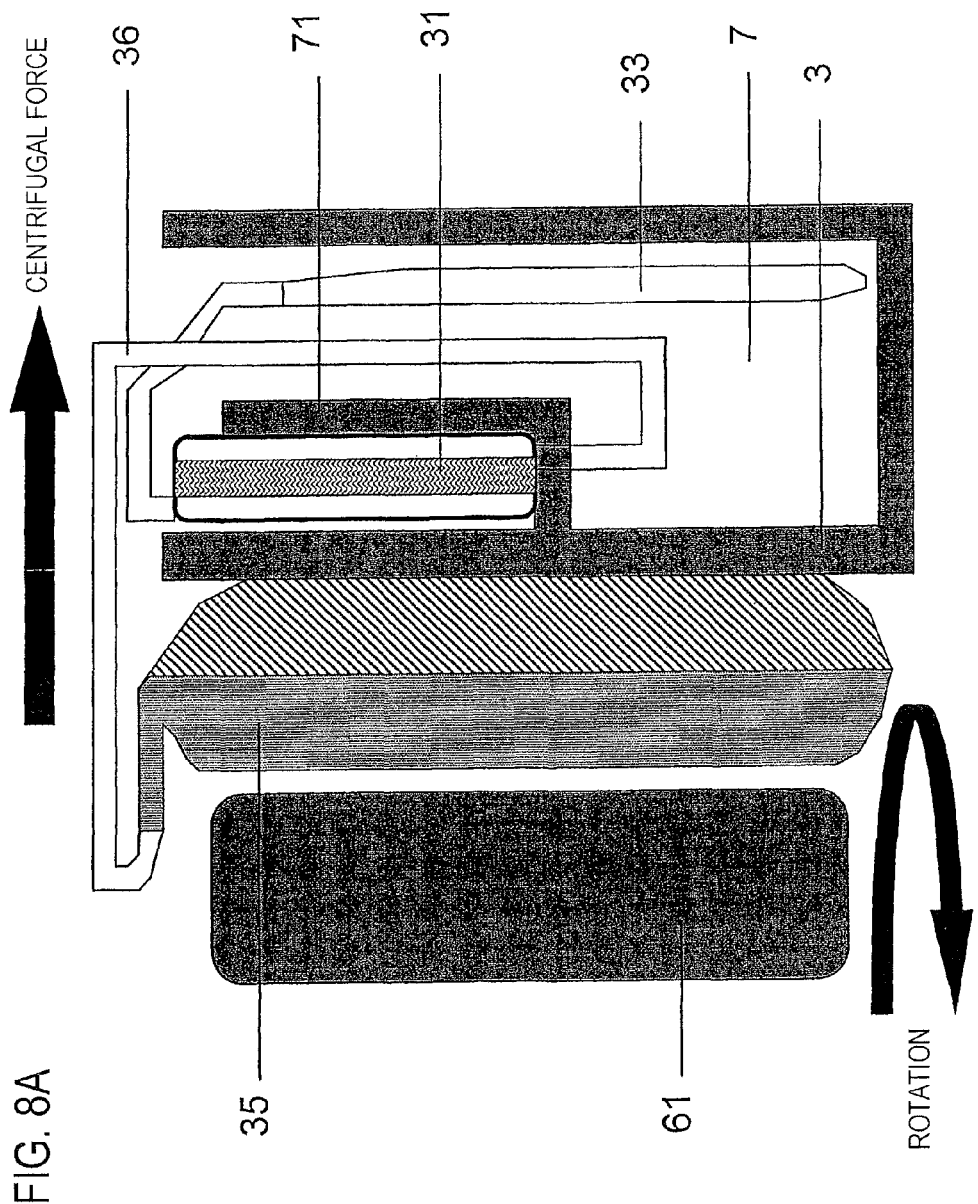
Figure 8B:
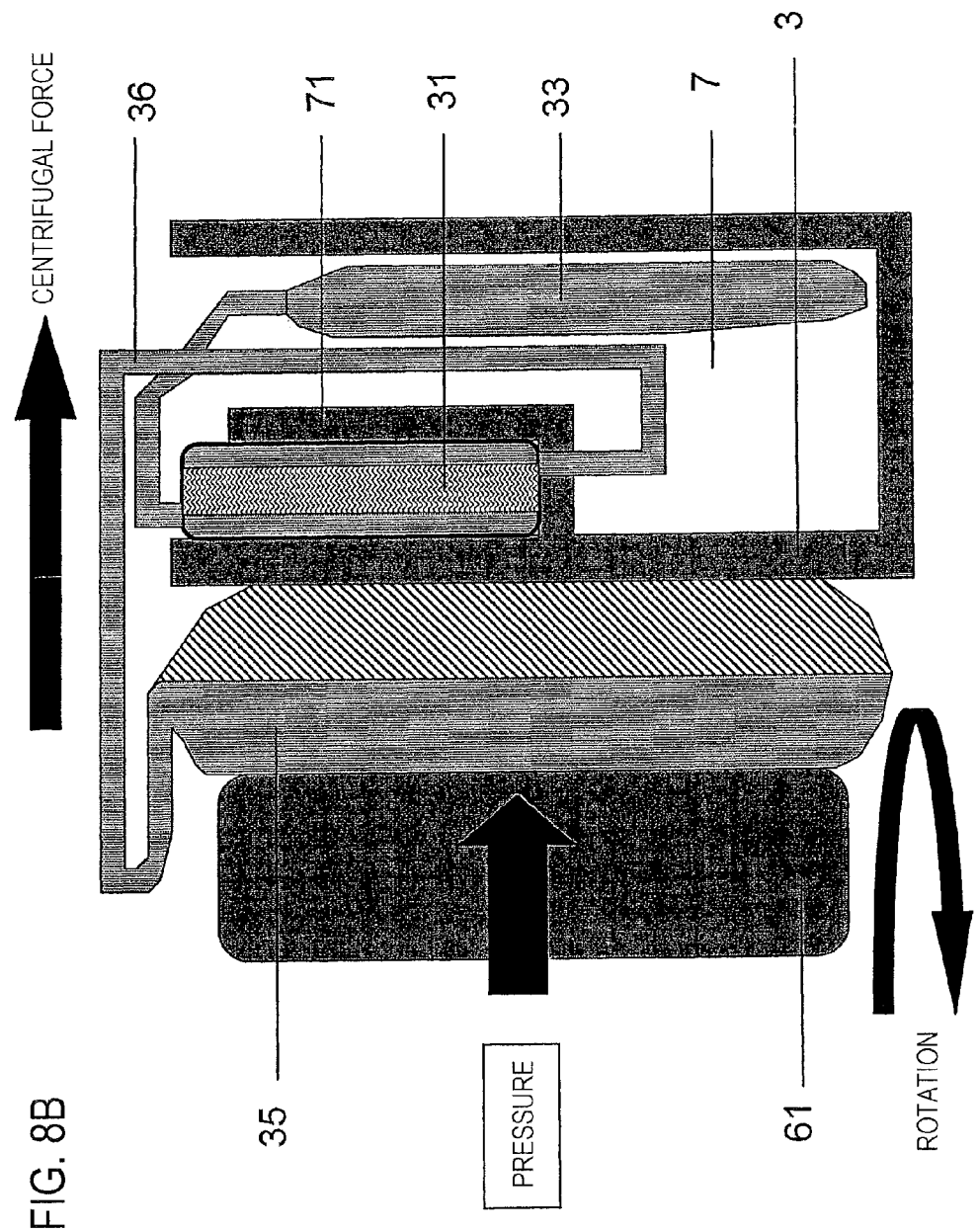

In the following an embodiment of the invention is described by means of the Figures showing the following:

FIG. 1 a top view of the cartridge according to the invention,

FIG. 2 a perspective view of the cartridge,

FIG. 3 a perspective view of the cartridge, sectioned along a symmetry line,

FIG. 4 a sectional perspective view of the cartridge supplementing the view of FIG. 4, FIG. 5 a further perspective and sectional view of the cartridge, FIG. 6 a bottom surface of a cover of the cartridge, FIG. 7 a perspective view of an accommodating box, FIGS. 8a to 8c schematic sectional views of the cartridge, from which the cell isolation can be seen, and FIG. 9 shows the flow of the blood product through the filter.

WAY(S) TO CARRY OUT THE INVENTION

An embodiment of the invention is described by means of FIGS. 1 to 9.

A cartridge 1 essentially consists of a partition wall 3 and a cover 9. The partition wall defines a blood bag section 5 and a product bag section 7. When the cartridge 1 is inserted into a system box 89 of the rotor of a centrifuge, the blood bag section 5 is located radially inside of the partition wall 3, whereas the product bag section 7 is located radially outside of the partition wall 3. An accommodating box 89 according to the invention is designated as system box 89.

A cover 9 is provided above the blood bag section 5. It has an essentially rectangular shape and, in its closed state, one of its longitudinal walls is in contact with the partition wall 3. In one corner point, the cover is pivotally mounted in the partition wall, whereas, in a second corner point, it is engaged with the partition wall 3 by means of a bolt 10. For opening the cover, pressure is applied onto the bolt 10 and then the cover is pivoted to the side. Thereby, the blood bag section 5 is freely accessible and can be filled with a blood bag 35.

By means of the simple pivoting mechanism a tube 36 and a blood bag 35 can quite easily be held in a desired position when the cover 9 is closed, and can be fixed in this predetermined position by closing the cover 9.

After the cover 9 has been closed it is possible to insert the tube 36 into the recesses 15, 19 which are formed in the top surface of the cover 9. A first photo sensor 25 is provided in the recess 15.

A tube clamp 34 in its closed state, which is delivered together with the blood bag and which is disposed on the tube, for example one produced by "Halkey Roberts", is accommodated in a recess 17 also formed in the top surface of the cover 9.

The end of the tube 36 which is the far end with respect to the blood bag 35 leads to the product bag section 7 where it is connected to a leukocyte filter 31 which is held in a fixture 29. The tube 36 is inserted into the leukocyte filter 31 radially from the outside and from below. The insertion of the filter 31 and the tube 36 is enabled by means of a slot 73 in an outside wall 71 of the fixture 29. Through the slot 73, the tube 36 connected to the filter 31 can be displaced from top to bottom when the filter is inserted into the fixture, such that the tube leads to the filter radially from the outside and from below.

Behind the filter 31, the tube 36 leads, via second recesses 75, 79, 81, 83 which are provided in the cover 9 and which are essentially positioned in a mirror-image manner relative to the recesses 15, 17, 19 to the product bag 33, which is located radially outside of the fixture 29.

A second tube clamp 34 is provided in the recess 81. A second photo sensor 85 is located in the recess 79.

Inside the cover 9, two rods 21, 23 as operating device for operating the clamps 34 are respectively led through the cover such that one of their ends protrudes slightly from a side surface 8 of the cover 9, which is located opposite the partition wall 3, and the other end is located in the area of the recess 17 accommodating the clamp 34. By applying a pressure onto one of the ends protruding from the side surface 8, the customary clamp 34 can thus be opened and closed. According to the embodiment, the tube clamps 34 can be operated individually as well as pneumatically.

After the cartridge 1 has been loaded, the cartridge 1 can be inserted into the system box 89 of the rotor of a centrifuge. When this is done, the side surface 8 of the cover 9 which is located opposite the partition wall 3 rests on a support 57 of the system box 89, which is provided in the area of a hub of the centrifuge. Moreover, at the support 57, there is a rod-shaped locking element 55 which has a projection 56 at its radial outside. By means of inserting the cartridge 1, the side surface 8 of the cover 9 slides over the projection 56 and moves the locking element 55 radially inward until the side surface 8 is positioned below the projection 56 and the locking element 55 springs back to its original position and thus prevents an upward displacement of the cartridge 1. Now the cartridge 1 is firmly positioned between the outside wall of the system box 89 and the support.

According to the embodiment, the rotor of the centrifuge is designed for six system boxes 89 having one cartridge 1 each. After all cartridges 1 have been inserted, the centrifuge is started. By means of the centrifugal force, the desired separation of the blood components is effected. Since the "buffy coat" diluted by an additive solution is in the blood bag 35, its lighter components will remain radially inside, whereas heavier components, i.e. the red blood cells collect outside.

In order to transport the desired blood component—according to the embodiment, these are the platelets—in high quality, i.e. without the admixture of other blood cells, from the blood bag, the separation of the components will be followed by a slight pressure being applied onto the blood bag by means of a known pressure pad 61, so that, after the clamps 34 have been opened, the solution rich in platelets begins to rise into the tube 36 leading upwards and radially inwards. The solution rich in platelets is led through the tube 36 into the leukocyte filter 31 into which it enters radially from the outside and from below.

In the leukocyte filter 31, the undesired leukocytes, i.e. the white blood cells, are removed. Due to the arrangement according to the invention of the tube 36 having the filter 31, the filtration is effected against the centrifugal force. Thus, heavier blood components, such as unintentionally fed red blood cells, are trapped in a front-end chamber of the filter, positioned radially outwards.

After having passed the leukocyte filter 31, the solution rich in platelets continues flowing through the tube 36 into a product bag 33, in which it is collected. Preferably, the product bag 33 is already formed as final storage bag for the product. The entire process is schematically illustrated in FIGS. 8a to 8c.

In order to remove any air that might be present in the filter, the flow speed is kept low for a certain volume quantity at the beginning of the product transfer, and thus it is enabled that the filter fills reliably and completely with the blood product. After the transfer of this predetermined volume quantity, the transport speed for a specific second volume quantity is increased by means of an appropriate control of the pressure pad. While this second volume is transported, there is hardly any risk that red blood cells contaminate the blood product (here: the thrombocyte concentrate). In case this nevertheless happens, this small number of red blood cells is collected in the lower and outer areas of the filter, due to the feeding of the tube 36 from radially outside and below into the filter and due to the effect of the centrifugal force.

After the second volume has been transferred, the first photo sensor is activated and the flow speed of the blood product in the tube 36 is reduced.

When the first photo sensor 25 detects a predetermined proportion of red blood cells in the thrombocyte-rich solution, it outputs a signal by means of which the flow speed is again reduced. Furthermore, the second photo sensor 85 arranged behind the filter 31 is activated.

During this phase, also a rather large number of red blood cells can enter into the filter 31 and even pass through it, until the second photo sensor 85 detects a predetermined proportion of red blood cells in the blood product and outputs a signal for terminating the cell isolation process. By means of this signal, the tube clamps 34 are closed by means of activating the rod 23, so that the red blood cells in the filter are reliably separated from the thrombocyte concentrate in the product bag. The operation of the rod is effected by means of an actuating mechanism provided in the system box 89.

As an alternative to the termination by means of the second photo sensor 85, the cell isolation process can also be terminated after a certain period of time has elapsed after the second photo sensor 85 has been activated.

In the embodiment, altogether six cartridges are provided in the centrifuge. The above described control of the cell isolation process in a cartridge 1 by means of a pressure pad 61, the opening and closing of the tube clamps 34 and the process control by means of the two photo sensors 25, 85 enables a continued cell isolation in the cartridges of the other system boxes 89, since the described process control operates individually for each combination of cartridge and system box.

For the transmission of the control and other electrical signals, an electric contact pad in the form of individual contact points 59 is provided at the support 57 of the system box 89. At the bottom surface of the cover 9, contact surfaces 27 assigned to the contact points 59 are provided and get into contact with the contact points 59 when the cartridge 1 is inserted into the system box. For this purpose, the contact points 59 are spring-mounted.

For the purpose of an easier handling, on the one hand, and in case blood components should escape due to a damage of the bags 33, 35, the tube 36 or the filter 31, the cartridge 1 is inserted into a collecting tank 87 from a radially inward direction. In case of a damage, the escaping blood component is largely collected in the collecting tank so that there would only be little contamination of the system box 89 or of the rotor itself. In such a case, the system box 89 can be easily dismounted from the rotor.

After the cell isolation has been terminated, each of the cartridges 1 is removed by applying a slight pressure onto the locking element 55 in order to move this radially to the inside.

Simultaneously, the cartridges 1 are seized at the finger holes 88 of the collecting tank 87, lifted upwards out of the system box 89 of the centrifuge, and are immediately replaced by new freshly loaded cartridges 1. During the subsequent cell isolation, the blood bags 35 and the product bags 33 can be removed from the exchanged cartridges 1 and these can be reloaded.

The invention relates to a cartridge (1) for accommodating blood bags (35), which is provided for the separation of blood components for the application in a centrifuge. The cartridge (1) has a partition wall (3) which separates a blood bag section (5) which is positioned radially inside from a product section (7) positioned radially outside, and a cover (9) disposed in a mounting position above the blood bag section (5). The cover (9) is connected to the partition wall (3) pivotally in a first point (11) and detachably in a second point (13), so that the blood bag section (5) is freely accessible by means of laterally pivoting the cover (9) out of the way. The cartridge is applicable in the rotor of a centrifuge.

The invention claimed is:

1. A cartridge for accommodating a set of bags fluidly connected by at least one tube, said cartridge to be used in a centrifuge for separation of blood components, the cartridge being adapted to be removably mounted in a rotor of the centrifuge, said cartridge comprising
   a blood bag section;
   a product section;
   a partition wall which separates the blood bag section of the removable cartridge from the product section, and
   a cover coupled to the removable cartridge above the blood bag section, wherein the cover is connected to the removable cartridge pivotally at a first point on said cartridge and detachably at a second point on said cartridge, so that the blood bag section is freely accessible by means of laterally pivoting the cover from the blood bag section and wherein said cover has a top surface and a bottom surface as defined when the cover is detached from the second point and pivoted to an open position and further comprising at least one recess for holding said at least one tube, said recess being formed in said top surface of the cover.

2. A cartridge according to claim 1, wherein an operating device is provided in the cover for operating a tube clamp disposed on said tube.

3. A cartridge according to claim 2, wherein the operating device protrudes from the cover at a side surface located opposite the partition wall when the cover is closed.

4. A cartridge according to claim 1, wherein a photo sensor is provided in the at least one recess.

5. A cartridge according to claim 1, wherein an electric connection means for electrical connection with the centrifuge is provided at a bottom surface of the cover.

6. A cartridge according to claim 1, wherein a fixture for receiving a filter fluidly connected by a tube to at least one of said bags of said set bags is provided adjacent said partition wall and outside of the blood bag section.

7. A cartridge according to claim 6, wherein the fixture comprises an outer wall positioned substantially parallel to the partition wall and having a guiding means for guiding the tube connected to said filter.

8. A cartridge according to claim 7, wherein the guiding means is a slot in the outer wall of the fixture.

9. A cartridge according to claim 6, wherein, a recess is provided at a top surface of the partition wall for guiding the tube connected to the filter from the fixture to at least one second recess in the top surface of the cover, and the second recess being configured to receive the tube and a tube clamp.

10. A cartridge according to claim 9, wherein the second recess is a mirror-image of said first recess with respect to a center line of said cover.

11. A cartridge according to claim 10, wherein the partition wall further comprises a passage at an upper edge of the partition wall for feeding the tube from the blood bag section to the product section.

12. A cartridge according to claim 2, wherein a first photo sensor is provided disposed in the at least one recess and a second photo sensor is disposed in an at least one second recess, and a second operating device is provided for operating a second tube clamp.

13. A cartridge according to claim 1, in further comprising a collecting tank positioned outside of and embracing the product section and parts of the blood bag section.

14. A cartridge according to claim 13, wherein the collecting tank is provided with a handling means for handling the cartridge.

15. The cartridge as in claim 1, wherein said cartridge is adapted to fit into one of a plurality of accommodating boxes surrounding a hub of a centrifuge rotor revolving about said hub, such that the cover extends away from said blood bag section towards said hub; and is adapted to engage a locking element connected to the hub of the rotor, the locking element being configured to lock the cartridge to the rotor.

16. A cartridge according to claim 15, wherein the bottom surface of the cover is adapted to contact a support at the hub of the cartridge and wherein the bottom surface of the cover is provided with a contact pad for establishing an electrically conductive connection between the rotor and the cartridge.

17. A cartridge according to claim 15, wherein a side surface of the cover is adapted to engage the locking element, the side surface being located opposite the partition wall.

18. A cartridge according to claim 15, wherein said product section is open opposite said partition wall such that a pressing element can be displaced outward from the hub of the centrifuge for applying pressure onto a blood bag in the cartridge, the pressing element being located proximate to the hub.

19. The removable cartridge of claim 1 wherein the cover further comprises a recess configured to receive a customary clamp.

20. The removable cartridge of claim 19, further comprising: at least one rod led through said cover, said rod having a first end protruding from a side surface of said cover and a second end protruding into said recess for said clamp, whereby said rod is adapted to open and close said clamp in said recess.

* * * * *